US00PP24247P3

(12) United States Plant Patent
Olesen

(10) Patent No.: US PP24,247 P3
(45) Date of Patent: Feb. 18, 2014

(54) CLIMBING ROSE PLANT NAMED 'POULCY021'

(50) Latin Name: ***Rosa* hybrid**
Varietal Denomination: Poulcy021

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 30 days.

(21) Appl. No.: 13/507,035

(22) Filed: May 31, 2012

(65) Prior Publication Data

US 2013/0326740 P1 Dec. 5, 2013

(51) Int. Cl.
*A01H 5/00* (2006.01)

(52) U.S. Cl.
USPC ..... Plt./113

(58) Field of Classification Search
USPC ..... Plt./113, 114, 115, 112
See application file for complete search history.

*Primary Examiner* — Kent L Bell

(57) ABSTRACT

A new garden rose plant of the Climbing class which has abundant, pink-apricot blend flowers and attractive foliage. This new and distinct variety has shown to be uniform and stable in the resulting generations from asexual propagation.

1 Drawing Sheet

Botanical designation: *Rosa* hybrid.
Variety denomination: 'Poulcy021'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2003 and the resulting seeds were planted in a controlled environment in Fredensborg, Denmark. The new variety, named 'Poulcy021', originated as a single seedling from the stated cross.

The new variety may be distinguished from its male pollen parent and female seed parent primarily by flower coloration and growth habit.

The objective of the hybridization of this rose variety was to create a new and distinct variety for garden use with unique qualities, such as:

1. Uniform and abundant pink-apricot blend flowers;
2. Vigorous, but compact growth when propagated both as a budded rose and on its own roots;
3. Exceptional disease resistance;
4. Reduced apical dominance in flowering habit. The new variety consistently produces flowers evenly from the lower branches to the top of the plant.

This combination of qualities is not present in previously available commercial cultivars of this type, known to the inventor, and distinguish 'Poulcy021' from all other varieties of which we are aware.

As part of the rose development program, Mogens N. Olesen germinated the seeds from the aforementioned hybridization during winter of 2003 and conducted evaluations on the resulting seedlings in a controlled environment in Fredensborg, Denmark. 'Poulcy021' was selected in the spring of 2004 by the inventor as a single plant from the progeny of the aforementioned hybridization.

Asexual reproduction of 'Poulcy021' by traditional budding and rooted cuttings was first done by Mogens N. Olesen in the nursery in Fredensborg, Denmark in July, 2004. This initial and other subsequent asexual propagations conducted in controlled environments have demonstrated that the characteristics of 'Poulcy021' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulcy021'. Specifically illustrated in the drawing are flowers at various stages of development, flower in parts, leaves, and stems.

DETAILED DESCRIPTION OF THE VARIETY

The following is a description of 'Poulcy021', as observed in its growth in a field nursery in Marion County, Oreg. Observed plants are 3 years of age, and were grown on their own roots. Color references are made using The Royal Horticultural Society (London, England) Colour Chart, 2001, except where common terms of color are used.

For a comparison, several physical characteristics of the rose variety 'Poulyc003', U.S. Plant Pat. No. 15,106 are compared to 'Poulcy021' in Chart 1.

CHART 1

| | 'Poulcy021' | 'Poulyc003' |
|---|---|---|
| Petal Count | 35 | 70 to 80 |
| Flower Diameter | 60 to 65 mm | 40 mm |
| General Tonality of Flower Color | Blend of Orange Group 27A and 29C with intonations of Yellow-Orange Group 19D. | Yellow-Orange Group 14D |

FLOWER AND FLOWER BUD

Blooming habit: Continuous.

Flower bud:

*Size*.—Upon opening, 22 mm in length from base of receptacle to end of bud. Bud diameter is 14 mm.

*Bud form*.—Ovoid.

*Bud color*.—As sepals divide petals are Orange Group 29C with intonations of Yellow-Orange Group 22A and Yellow Group 4A.

*Sepal inner surface*.—Color: Green Group 138B. Surface: Smooth and moderately pubescent.

*Sepal outer surface*.—Color: Yellow-Green Group 146A. Texture: Smooth and many stipitate glands.

*Sepal shape*.—Apex: Cirrhose. Base: Flat at union with receptacle.

*Sepal margin*.—Margins have very strong foliaceous appendages on three of the five sepals.

*Sepal size*.—35 mm long by 10 to 15 mm wide.

*Receptacle*.—Texture: Smooth. Size: 7 mm in height by 7 mm wide. Color: Yellow-Green Group 146A. Shape: Campanulate.

*Pedicel*.—Surface: Smooth. Length: 20 to 35 mm. Diameter: 3 mm on average. Color: Yellow-Green Group 144B. Strength: Strong.

*Peduncle*.—Length: 3 to 18 cm. Diameter: 3 to 4 mm. Color: Yellow-Green Group 144B with Greyed-Red Group 182A.

Flower bud development: Flower buds are borne in clusters of 5 flower buds per stem, resembling a panicle. Reduced apical dominance in flower habit causes flower buds to develop evenly from the base of the plant to the upper branches.

Flower bloom:

*Fragrance*.—Moderate rose perfume.

*Duration*.—The blooms have a duration on the plant of approximately 10 days. Petals fall cleanly away from plant after flowers have fully matured.

*Size*.—Flower diameter is 60 to 65 mm when open. Flower depth is 30 mm.

*Flower shape*.—General shape is an open cup with petals that curve out from the center.

*Shape of flower, side view*.—Upon opening the upper portion is flat and the lower portion is flat.

Petalage: Under normal conditions, flowers have 35 petals total, 2 or 3 of which are petaloids.

General tonality of flower: Open flowers are Blend of Orange Group 27A and 29C with intonations of Yellow-Orange Group 19D. Tonality changes to Yellow Group 11D and Red Group 36C as the flower ages.

Petal color:

*Upon opening, outer petals*.—Upper surface: Yellow Group 9B at the petal base. Yellow Group 10 B at the middle zone. Orange Group 27B at the margins. Lower surface: Red Group 36A with basal intonations of Yellow Group 8B.

*Upon opening, inner petals*.—Upper surface: Yellow-Orange Group 19A and 19B with intonations of Yellow Group 9B at the petal base. Lower surface: Orange Group 24C with intonations of Yellow Group 11A at the petal base.

*After opening, inner and outer petals*.—Upper surface: Blend of Orange Group 27C and Red Group 36A with marginal intonations of Yellow Group 2C. Lower surface: Red Group 36B with light intonations of Red Group 56B. Basal intonations are Yellow Group 10C.

Petals:

*Petal reflex*.—Weak.

*Margin*.—Entire and uniform with weak to no undulations of margin.

*Shape*.—Generally narrow elliptic. Apex shape: Rounded. Base shape: Acute.

*Size*.—30 mm (l)×25 mm (w).

*Texture*.—Smooth.

*Thickness*.—Average.

Petaloids:

*Size*.—20 mm (l) by 15 mm (w).

*Quantity*.—2 or 3.

*Shape*.—Asymmetric. Rounded at the apex and acute at the base.

*Color*.—Blend of Orange Group 27C and Red Group 36A with marginal intonations of Yellow Group 2C on the upper surface. The lower surface is Red Group 36B with light intonations of Red Group 56B. Basal intonations are Yellow Group 10C.

Reproductive organs:

*Pollen*.—None observed.

*Anthers*.—Size: 3 mm in length. Color: Yellow Group 10C. Quantity: 60 on average.

*Filaments*.—Color: Yellow Group 12A. Length: 6 mm.

*Pistils*.—Length: 5 mm. Quantity: 40 on average.

*Stigmas*.—Color: Greyed-Orange Group 163D.

*Styles*.—Color: Yellow-Green Group 145D.

*Location of stigmas*.—Inferior in location relative to the length of the filaments and the height of the anthers.

*Hips*.—None Observed.

PLANT

Plant growth: Arching habit. Plants are 100 cm in height, and 100 cm wide.

Stems:

*Color*.—Juvenile growth: Yellow-Green Group 146C with Greyed-Purple Group 183C. Mature growth: Yellow-Green Group 144A.

*Length*.—On average, canes are 65 cm from the base of the plant to the flowering portion.

*Diameter*.—8 mm.

*Internodes*.—On mature canes, there is an average distance of 40 mm between nodes.

*Surface texture*.—Young wood: Smooth. Older wood: Smooth.

Long prickles:

*Incidence*.—6 prickles per 10 cm of stem.

*Size*.—Average length of prickles on mature stems is 8 mm.

*Shape*.—Upper portion is linear. Lower portion is concave.

*Color*.—Juvenile prickles: Greyed-Purple Group 185A. Mature prickles: Greyed-Yellow Group 162A.

Plant foliage:

*Compound leaf*.—140 mm (l)×95 mm (w).

*Quantity*.—2 leaves per 10 cm of stem on average.

*Leaf bearing angle to the stem*.—45 degrees.

*Color of juvenile foliage*.—Upper side: Yellow-Green Group 146A. Lower side: Yellow-Green Group 146B with intonations of Greyed-Purple Group 183C.

*Color of mature foliage*.—Upper side: Yellow-Green Group 147A. Lower side: Yellow-Green Group 147B.

Plant leaves and leaflets:

*Stipules*.—Size: 20 mm in length. Quantity: 2 per compound leaf. Shape: Linear, slightly broad based with outward extending apices. Margins: Finely serrated with many stipitate glands. Color: Green Group 137A.

*Petiole*.—Length: 30 mm. Diameter: 2 mm.

*Upper surface*.—Color: Yellow-Green Group 144A with Greyed-Red Group 182A.

*Lower surface*.—Color: Yellow-Green Group 144D.

*Rachis*.—Length: 40 mm. Upper surface: Color: Yellow-Green Group 144A with Greyed-Red Group 182A.

*Lower surface*.—Color: Yellow-Green Group 144D.

*Leaflet*.—Quantity: Normal number of leaflets per leaf in middle of the stem is 7 leaflets. Margins: Serrated. Size: Average size of the terminal leaflet on normal leaves is 55 mm in length by 35 mm wide. Shape: Generally elliptical. Base: Rounded. Apex: Acute. Texture: Smooth. Thickness: Average. Arrangement: Odd pinnate. Venation: Reticulate. Glossiness: None.

Disease resistance: Above average resistance to powdery and downy mildew, rust, black spot, and Botrytis under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the Climbing rose class named 'Poulcy021', substantially as illustrated and described herein, due to its abundant pink-apricot blend flowers, disease resistance, and extended period of bloom.

* * * * *

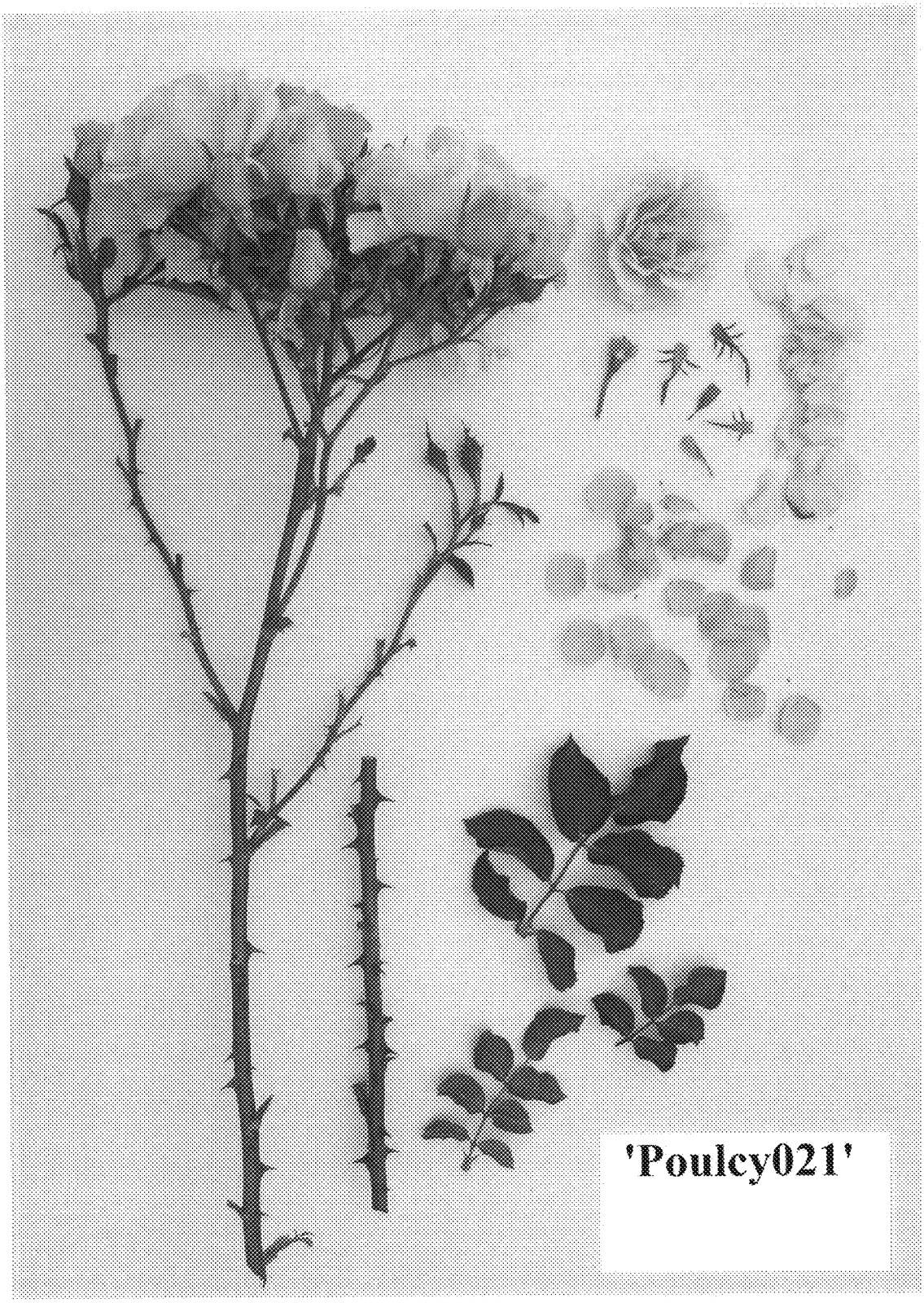
'Poulcy021'